United States Patent
Vautravers et al.

(10) Patent No.: US 9,796,654 B2
(45) Date of Patent: Oct. 24, 2017

(54) PROCESS FOR THE DIMERIZATION OF ACTIVATED OLEFINS

(71) Applicant: BASF SE, Ludwigshafen (DE)

(72) Inventors: Nicolas Vautravers, Mannheim (DE); Joaquim H. Teles, Waldsee (DE); Albrecht Berkessel, Erftstadt (DE); Mathias Paul, Köln (DE); Veera R. Yatham, Köln (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/312,033

(22) PCT Filed: May 19, 2015

(86) PCT No.: PCT/EP2015/060985
§ 371 (c)(1),
(2) Date: Nov. 17, 2016

(87) PCT Pub. No.: WO2015/177141
PCT Pub. Date: Nov. 26, 2015

(65) Prior Publication Data
US 2017/0107168 A1    Apr. 20, 2017

(30) Foreign Application Priority Data

May 20, 2014   (EP) .................................... 14169141

(51) Int. Cl.
*C07C 67/00*    (2006.01)
*C07C 67/347*   (2006.01)
*B01J 31/02*    (2006.01)

(52) U.S. Cl.
CPC ......... *C07C 67/347* (2013.01); *B01J 31/0244* (2013.01); *B01J 2231/20* (2013.01)

(58) Field of Classification Search
CPC . B01J 2231/20; B01J 31/0244; C07C 67/347; C07C 69/593
See application file for complete search history.

(56) References Cited

U.S. PATENT DOCUMENTS

| 4,451,665 A | 5/1984  | Nugent       |
|-------------|---------|--------------|
| 4,594,447 A | 6/1986  | Wilke et al. |
| 5,585,496 A | 12/1996 | Teles et al. |

FOREIGN PATENT DOCUMENTS

| DE | 3336691 A1 | 4/1985 |
| EP | 0587044 A2 | 3/1994 |

OTHER PUBLICATIONS

Kato, T., et al., ("Cooperative N-Heterocyclic Carbene/Bronsted Acid Catalysis for the Tail-to-Tail (Co)dimerization of Methacrylonitrile", Journal of Organic Chemistry, vol. 79, No. 10, pp. 4484-4491, Published Apr. 28, 2014).*

Biju, A., et al., "N-Heterocyclic Carbene Catalyzed Umpolung of Michael Acceptors for Intermolecular Reactions", Angewandte Chemie International Edition, vol. 50, No. 36, (2011), pp. 8412-8415.

International Preliminary Examination Report with Annexes (in English) for PCT/EP2015/060985 mailed Aug. 3, 2016.

International Search Report for PCT/EP2015/060985 mailed Jul. 27, 2015.

Kato, T., et al., "Cooperative N-Heterocyclic Carbene/Bronsted Acid Catalysis for the Tail-to-Tail (Co)dimerization of Methacrylonitrile", Journal of Organic Chemistry, vol. 79, No. 10, (2014), pp. 4484-4491.

(Continued)

*Primary Examiner* — Jafar Parsa
*Assistant Examiner* — Blaine G Doletski
(74) *Attorney, Agent, or Firm* — Drinker Biddle & Reath LLP

(57) ABSTRACT

The present invention relates to a process for the preparation of compounds or a mixture of compounds of the general formulae I.a or I.b

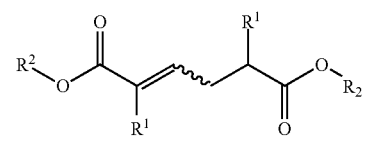

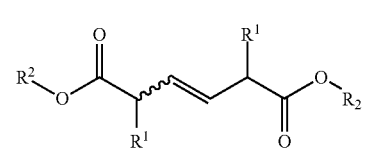

wherein
$R^1$ is selected from $C_1$-$C_{12}$-alkyl, $C_3$-$C_6$-cycloalkyl, —C(=O)OR$^2$, —PO(OR$^{2a}$)$_2$, aryl and hetaryl,
$R^2$, $R^{2a}$ are independently of each other selected from the group consisting of hydrogen, $C_1$-$C_{12}$-alkyl, $C_1$-$C_{12}$-alkenyl, where the last two radicals mentioned are unsubstituted, partly or completely halogenated or substituted by 1, 2, 3 or 4 radicals selected from the group consisting of $C_1$-$C_6$-alkoxy and CN, $C_3$-$C_6$-cycloalkyl, $C_3$-$C_6$-cycloalkyl-$C_1$-$C_4$-alkyl, aryl and aryl-$C_1$-$C_4$-alkyl, where the last four radicals mentioned are unsubstituted or substituted by 1, 2, 3 or 4 radicals selected from the group consisting of $C_1$-$C_6$-alkyl, $C_1$-$C_6$-haloalkyl, $C_1$-$C_6$-alkoxy, $C_1$-$C_6$-haloalkoxy, —CN, and halogen,
which comprises dimerizing olefin compound of the general formula II,

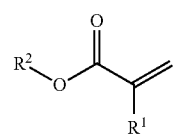

in the presence of at least one N-heterocyclic carbene catalyst.

17 Claims, No Drawings

(56) References Cited

OTHER PUBLICATIONS

Matsuoka, S., et al., "Organocatalytic Tail-to-Tail Dimerization of Olefin: Umpolung of Methyl Methacrylate Mediated by N-Heterocyclic Carbene", Orgnaic Letters, vol. 13, No. 14, (2011), pp. 3722-3725.

* cited by examiner

PROCESS FOR THE DIMERIZATION OF ACTIVATED OLEFINS

CROSS-REFERENCE TO RELATED APPLICATIONS

This application is a national stage application (under 35 U.S.C. §371) of PCT/EP2015/060985, filed May 19, 2015, which claims benefit of European Application No. 14169141.0, filed May 20, 2014, both of which are incorporated herein by reference in their entirety.

The present invention relates to a process for the preparation of compounds or a mixture of compounds of the general formulae I.a or I.b

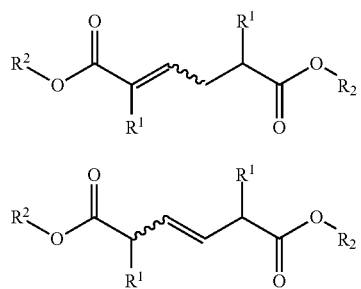

wherein
R$^1$ is selected from C$_1$-C$_{12}$-alkyl, C$_3$-C$_6$-cycloalkyl, —C(=O)OR$^2$, —PO(OR$^{2a}$)$_2$, aryl and hetaryl,
R$^2$, R$^{2a}$ are independently of each other selected from the group consisting of hydrogen, C$_1$-C$_{12}$-alkyl, C$_2$-C$_{12}$ alkenyl-, where the last two radicals mentioned are unsubstituted, partly or completely halogenated or substituted by 1, 2, 3 or 4 radicals selected from the group consisting of C$_1$-C$_6$-alkoxy and CN, C$_3$-C$_6$-cycloalkyl, C$_3$-C$_6$-cycloalkyl-C$_1$-C$_4$-alkyl, aryl and aryl-C$_1$-C$_4$-alkyl, where the last four radicals mentioned are unsubstituted or substituted by 1, 2, 3 or 4 radicals selected from the group consisting of C$_1$-C$_6$-alkyl, C$_1$-C$_6$-haloalkyl, C$_1$-C$_6$-alkoxy, C$_1$-C$_6$-haloalkoxy, —CN, and halogen,
which comprises dimerizing olefin compound of the general formula II,

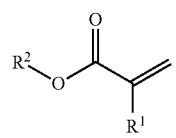

in the presence of at least one N-heterocyclic carbene catalyst,

BACKGROUND OF THE INVENTION

The dimerization of functionalized olefins is an important chemical reaction, which allows the efficient production of unsaturated compounds or building blocks having multiple functional groups.

The dimerization of functionalized olefins, e.g. Michael acceptors, is generally known in the state of the art. Typically, transition metal complexes such as Ni-, Ru-, Rh- or Pd-complexes are used to catalyze this reaction.

DE 3336691 for example discloses a process for the nickel catalyzed dimerization of acrylic acid derivatives to yield linear unsaturated dicarboxylic acids and the use of these dimethylcarboxylic acid derivatives as monomers and/or co-monomers in poly-mer, polycondensation and hydration reactions.

U.S. Pat. No. 4,451,665 discloses a process for dimerizing a lower alkylacrylate or a lower alkyl-methacrylate in the presence of a palladium (II) catalyst to yield mixtures of isomeric linear dimers. In particular, this reaction was used for the preparation of mixtures of linear isomeric dimethyl hexenedioates and dimethyl 2,5-dimethylhexenedioates.

The dimerization products are typically obtained as mixtures of several individual isomers. The overall yields of the dimerization products are usually limited due to the formation of side products.

It is further known in the state of the art that the selective tail-to-tail dimerization of functionalized olefins can be achieved using N-heterocyclic carbenes (NHCs) as the catalyst providing the dimerization products in good yields and selectivities.

Biju et al., Angew. Chem. Int. Ed. Engl. 2011, Vol. 50(36), pp. 8412-5, disclose a process for the coupling of two activated olefins in the presence of an N-heterocyclic carbene catalyst (NHC-catalyst) and the organic base 1,8-Diazabicyclo[5.4.0]undec-7-en (DBU). Specifically, the dimerization reactions are performed in 1,4-dioxane using 10 mol-% of protonated NHC-catalyst as a perchlorate salt and 1.0 equivalent of DBU. The reaction mixture is heated to 80° for 24 hours. The process of Biju et al. allows the selective production of several linear dimerization products in moderate to excellent yields and high E/Z ratios (up to 97:3).

Matsuoka et al., Org. Lett. 2011, Vol. 13(14), pp. 3722-5, disclose a process for the selective tail-to-tail dimerization of substituted acrylates, in particular of methyl methacrylate, in the presence of an N-heterocyclic carbene catalyst. Specifically, the dimerization reactions are performed in the absence of any solvent or in the presence of toluene using 10 mol-% of free NHC-catalyst and by heating the reaction mixture to 80° for 8 or 24 hours, yielding the linear dimerization products in good to excellent yields and E/Z ratios in the range of 88:12 to 98:2.

The reaction mechanism of the NHC-catalyzed tail-to-tail dimerization of substituted acrylates was later identified by the same authors and is described in Kato et al., J. Org. Chem. 2013, Vol. 78(17), pp. 8739-8747.

Kato et al., J. Org. Chem. 2014, Vol. 79(10), pp. 4484-4491, disclose a process for the tail-to-tail dimerization of methacrylonitrile as well as the co-dimerization of methacrylonitrile with n-butyl methacrylate in the presence of an N-heterocyclic carbene catalyst and an alcohol additive. Specifically, methacrylonitrile was dimerized either in the presence of 5 mol-% of an NHC-catalyst and 5 to 50 mol-% of a lower alkyl alcohol or an aromatic alcohol as additive, or in the presence of a mixture of 5 to 50 mol-% of a lower alkyl alcohol and 0.5 to 1 mol-% of an aromatic alcohol as additive. The reactions were carried out in bulk or by adding an external solvent such as 1,4-dioxane. Their experiments reveal that aromatic alcohols, such as 2-naphthol or hydroquinone, are significantly less suitable to accelerate the investigated dimerization reactions, than lower alkyl alcohols, such as isopropanol or n-butanol. The authors further report that, in contrast to the dimerization of methacrylonitrile, the addition of an alcohol additive to the NHC-catalyzed dimerization of n-butyl methacrylate has detrimental effects on the reaction rate and yield.

However, long reaction times and large amounts of catalyst are generally needed to achieve high yields and selectivities. Thus, there is a need to further improve the NHC-catalyzed selective tail-to-tail dimerization of functionalized olefins.

SUMMARY OF THE INVENTION

The object of the present invention is to provide an improved process for the selective tail-to-tail dimerization of functionalized olefins, which allows a more efficient production of the dimerization products. More specifically, the object of the present invention is to improve the reaction rate of the selective tail-to-tail dimerization of 1,1-difunctionalized olefins catalyzed by N-heterocyclic carbenes (NHCs) in order to increase the space-time yield and to decrease the amount of NHC-catalyst needed.

It was surprisingly found that compounds or a mixture of compounds of the general formulae I.a or I.b, as defined above, can efficiently be obtained in high yields and selectivities by a process, which comprises dimerizing olefin compound of the general formula II, as defined above, in the presence of at least one N-heterocyclic carbene catalyst and at least one additive having at least one proton donating functional group, where the additive is used in an amount of from 0.005 to 4 mol-%, based on the total amount of compound (II) in the reaction mixture, and where the proton-donating functional group has a pKa-value in water at 25° C. in the range of from 4 to 14, preferably in the range of from 7 to 13, to yield a compound of the general formulae I.a or I.b or a mixture thereof.

Hence, the present invention relates to a process for the preparation of compounds or a mixture of compounds of the general formulae I.a or I.b, which comprises dimerizing olefin compound of the general formula II, in the presence of at least one N-heterocyclic carbene catalyst and at least one additive having at least one proton donating functional group, where the additive is used in an amount of from 0.005 to 4 mol-%, based on the total amount of compound (II) in the reaction mixture, and where the proton-donating functional group has a pKa-value in water at 25° C. in the range of from 4 to 14, preferably in the range of from 7 to 13.

The process according to the present invention exhibits the following advantages:
- The space-time yields for the preparation of compounds of the general formulae I.a and I.b could be dramatically improved compared to the processes known in the state of the art.
- The amount of NHC-catalyst that are necessary to obtain compounds I.a and I.b in high yields and selectivities could be significantly decreased compared to the processes known in the state of the art.
- The present process for producing compounds of the general formulae I.a and I.b is simple and efficient. Compounds I.a and I.b can therefore be provided without difficulty on a large industrial scale.
- The present process can be used for the continuous production of compounds I.a and I.b.
- The process according to the present invention is applicable to a large scope of 1,1-disubstituted olefins, giving access to a vast number of different valuable dimerization products.

DETAILED DESCRIPTION

For the purpose of the present invention, the term "space-time yield" refers to the amount of desired product obtained, divided by the required reaction volume and the required time. It can be expressed either in kg per liter and hour ($kg*L^{-1}*h^{-1}$) or in mol per liter and hour ($mol*L^{-1}*h^{-1}$).

For the purposes of the present invention, the term "halogen" refers to fluorine, chlorine, bromine, and iodine. Preferably, halogen is fluorine and chlorine, in particular chlorine.

The term "$C_1$-$C_{12}$-alkyl" refers to linear or branched alkyl radicals containing 1 to 12 carbon atoms. Examples of $C_1$-$C_{12}$-alkyl are methyl, ethyl, propyl, isopropyl, n-butyl, isobutyl, sec-butyl, tert-butyl, n-pentyl, 2-pentyl, 2-methylbutyl, 3-methylbutyl, 1,2 dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 1-ethylpentyl, 2-ethylpentyl, 1-propylbutyl, 1-ethyl-2-methylpropyl, n-octyl, isooctyl, 2-ethylhexyl, n-nonyl, isononyl, 2-propylhexyl, n-decyl, isodecyl, 2-propylheptyl, n-undecyl, isoundecyl, n-dodecyl, isododecyl, and the like. It is particularly preferable that $C_7$-$C_{12}$-alkyl is n-octyl, n-nonyl, isononyl, 2-ethylhexyl, isodecyl, 2-propylheptyl, n-undecyl, isoundecyl and the like. Preferably, $C_1$-$C_{12}$-alkyl is selected from linear or branched alkyl groups having 1 to 10 carbon atoms, in particular 1 to 8 carbon atoms.

The term "$C_1$-$C_{12}$-alkyl" includes within its definition the terms "$C_1$-$C_6$-alkyl" and "$C_1$-$C_4$-alkyl".

The term "$C_3$-$C_6$-cycloalkyl" refers to the saturated alicyclic rings of 3 to 6 carbon atoms such as cyclopropyl, cyclobutyl, cyclopentyl, cyclohexyl, and the like.

For the purpose of the present invention, the term "$C_2$-$C_{12}$-alkenyl" refers to straight and branched radicals of 2 to 12 carbon atoms containing one or more, for example 1, 2 or 3 double bonds. Preferably, $C_2$-$C_{12}$-alkenyl is selected from straight and branched alkenyl groups with 2 to 8 carbon atoms, in particular with 2 to 6 carbon atoms containing 1 or 2 double bonds. Examples of preferable $C_2$-$C_{12}$-alkenyl are ethenyl, 1-propenyl, 2-propenyl, 1-methylethenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, penta-1,3-dien-1-yl, hexa-1,4-dien-1-yl, hexa-1,4-dien-3-yl, hexa-1,4-dien-6-yl, hexa-1,5-dien-1-yl, hexa-1,5-dien-3-yl, hexa-1,5-dien-4-yl, hepta-1,4-dien-1-yl, hepta-1,4-dien-3-yl, hepta-1,4-dien-6-yl, hepta-1,4-dien-7-yl, hepta-1,5-dien-1-yl, hepta-1,5-dien-3-yl, hepta-1,5-dien-4-yl, hepta-1,5-dien-7-yl, hepta-1,6-dien-1-yl, hepta-1,6-dien-3-yl, hepta-1,6-dien-4-yl, hepta-1,6-dien-5-yl, hepta-1,6-dien-2-yl, octa-1,4-dien-1-yl, octa-1,4-dien-2-yl, octa-1,4-dien-3-yl, octa-1,4-dien-6-yl, octa-1,4-dien-7-yl, octa-1,5-dien-1-yl, octa-1,5-dien-3-yl, octa-1,5-dien-4-yl, octa-1,5-dien-7-yl, octa-1,6-dien-1-yl, octa-1,6-dien-3-yl, octa-1,6-dien-4-yl, octa-1,6-dien-5-yl, octa-1,6-dien-2-yl and the like.

The term "$C_1$-$C_6$-alkoxy" refers to straight and branched alkoxy radicals having 1 to 6 carbon atoms, preferably 1 to 4 carbon atoms. Examples of preferable $C_1$-$C_6$-alkoxy radicals are methoxy, ethoxy, n-propoxy, isopropoxy, n-butoxy, tert-butoxy, and the like.

The term "$C_1$-$C_6$-alkoxy" includes within its definition the term "$C_1$-$C_4$-alkoxy"

The term "$C_1$-$C_6$-haloalkyl" refers to straight and branched $C_1$-$C_6$-alkyl radicals, wherein at least one hydrogen atom is substituted by halogen, preferably by fluorine, chlorine or bromine, in particular by fluorine or chlorine.

Examples of $C_1$-$C_6$-haloalkyl include fluoromethyl, difluoromethyl, trifluoromethyl, chloromethyl, dichloromethyl, trichloromethyl, pentafluoroethyl, 2-chloroethyl, heptafluoropropyl, heptafluoroisopropyl, 2-chloropropyl, 3-chloropropyl, nonafluorbuonafluorobutyl, nonafluoroisobutyl, 2-chlorobutyl, 3-chlorobutyl, 4-chlorobutyl, 1,1-dimethyl-2-chloroethyl, undecylfluoropentyl, undecylfluoroisopentyl and the like.

The term "$C_1$-$C_6$-haloalkyl" includes within its definition the term "$C_1$-$C_4$-haloalkyl".

The term "$C_1$-$C_6$-haloalkoxy" refers to $C_1$-$C_6$-alkoxy radicals, wherein at least one hydrogen atom of the alkyl moiety is substituted by halogen, preferably by fluorine, chlorine or bromine, in particular by fluorine or chlorine. Examples of $C_1$-$C_6$-haloalkoxy include fluoromethoxy, difluoromethoxy, trifluoromethoxy, chloromethoxy, dichloromethoxy, trichloromethoxy, pentafluoroethoxy, 2-chloroethoxy, heptafluoropropoxy, heptafluoroisopropoxy, 2-chloropropoxy, 3-chloropropoxy, nonafluorobutoxy, nonafluoroisobutoxy, 2-chlorobutoxy, 3-chlorobutoxy, 4-chlorobutoxy, 1,1-dimethyl-2-chloroethoxy and the like.

The term "aryl" refers to a polyunsaturated, aromatic moiety that can be a single ring or multiple rings, for example from 1 to 3 rings, which are fused together or linked covalently of and where at least one ring is aromatic. Examples of aryl include phenyl, 1-naphthyl, 2-naphtyl, 1,2,3,4-tetrahydronaphthyl, 4-biphenyl, indanyl, anthracyl, phenanthryl and the like.

The term "hetaryl" or "heteroaryl" refers to a polyunsaturated, aromatic moiety having 5 to 14 carbon atoms, preferably 5 to 6 carbon atoms, that can be a single ring or multiple rings, for example 1, 2, or 3 rings, which are fused together or linked covalently and where at least one ring carbon atom, for example 1, 2, 3 or 4 ring carbon atoms, are replaced by O, N or S. Examples of heteroaryl include furyl, thienyl, oxazolyl, isoxazolyl, thiazolyl, isothiazolyl, benzofuranyl, benzthiazolyl, benzimidazolyl, pyridyl, chinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl, carbazolyl and the like.

For the purpose of the present invention, the term "fused, unsaturated N-heterocycle" or "N-heterocycle" refers to fused mono-, di- or tricyclic aromatic moieties having 1 or 2 nitrogen atoms as ring members. Fused N-heterocylce include fused pyridine, fused pyrimidine, fused pyridazine, fused quinoline, fused isoquinoline, fused quinazoline, fused cinnoline, fused phthalazine, fused quinoxaline, fused phenanthridine, fused benzo[h]quinoline, benzo[h]isoquinoline and fused phenanthroline.

Preferably, the radical $R^1$ in formulae I.a, I.b or II is selected from unsubstituted $C_1$-$C_4$-alkyl and —$PO(OR^{2a})_2$, where $R^{2a}$ has one of the meanings given above.

Especially, the radical $R^1$ in formulae I.a, I.b or II is selected from unsubstituted $C_1$-$C_4$-alkyl, in particular methyl.

Further preferred are compounds, where the radical $R^2$ is selected from unsubstituted $C_1$-$C_6$-alkyl, in particular from unsubstituted $C_1$-$C_4$-alkyl.

Further preferred are compounds of the general formulae I.a, I.b or II in which both radicals $R^2$ are identical.

A preferred embodiment of the present invention relates to compounds of formulae I.a, I.b or II, wherein
  $R^1$ is selected from methyl and —$PO(OR^{2a})_2$ and
  $R^2$, $R^{2a}$ are independently of each other selected from unsubstituted $C_1$-$C_6$-alkyl.

A particularly preferred embodiment of the present invention relates to compounds of formulae I.a, I.b or II, wherein $R^1$ is methyl and
$R^2$ is selected from unsubstituted $C_1$-$C_4$-alkyl.

In a particularly preferred embodiment of the present invention, the compound of the general formula II is selected from methyl methacrylate, ethyl methacrylate and n-butyl methacrylate.

The preferred embodiments mentioned above may be combined arbitrarily with one another.

Accordingly, examples of preferred compounds of the general formula I.a are dimethyl 2,5-dimethyl-2-hexenedioate, diethyl 2,5-dimethyl-2-hexenedioate, di-(n-butyl) 2,5-dimethyl-2-hexenedioate, in particular dimethyl 2,5-dimethyl-2-hexenedioate.

Examples of preferred compounds of the general formula I.b are dimethyl 2,5-dimethyl-3-hexenedioate, diethyl 2,5-dimethyl-3-hexenedioate, di-(n-butyl) 2,5-dimethyl-3-hexenedioate, in particular dimethyl 2,5-dimethyl-3-hexenedioate.

Examples of preferred compounds of the general formula II are dimethyl 2,5-dimethylhexanedioate, diethyl 2,5-dimethylhexanedioate, di-(n-butyl) 2,5-dimethylhexanedioate, in particular dimethyl 2,5-dimethylhexanedioate.

The dimerization products of the general formulae I.a and I.b are typically obtained as stereoisomer mixtures comprising the E-isomers of the formulae I.a-E and I.b-E, respectively, and the Z-isomers of the formulae I.a-Z and I.b-Z, respectively.

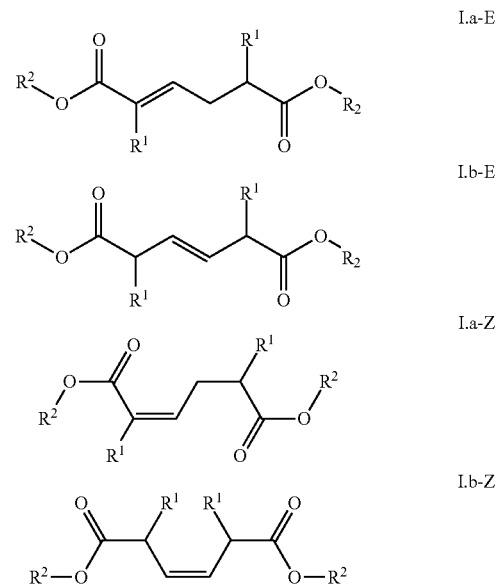

Often, the dimerization products of the general formulae I.a and I.b are obtained as E/Z-isomer mixtures, where one of the isomers is present in excess. In addition, the E/Z-isomers of compounds I.b (I.b-E and I.b-Z) are typically obtained in the form of diastereoisomer mixtures of their corresponding D/L- and meso-form. Typically, the D/L and meso-form are obtained in relative amount ranging from 10:1 to 1:10.

According to the present invention, the dimerization reaction is carried out in the presence of an additive having at least one proton donating functional group.

Typically, the proton-donating functional group of the additive has a pKa-value in water at 25° C. in the range of from 4 to 14, preferably in the range of from 7 to 13.

Preferably, the additive having a proton-donating functional group is selected from aromatic alcohols, halogenated aliphatic alcohols, protonated aliphatic amines and thiols.

Examples of preferred aromatic alcohols are phenol, 1-naphthol, 2-naphthol and substituted phenols, for example 2-methylphenol, 3-methylphenol, 4-methylphenol, 2-nitropheno, 3-nitrophenol, 4-nitrophenol, 2-methoxyphenol, 3-methoxyphenol, 4-methoxyphenol, 2,6-dimethoxyphenol, 4-chloro-3-methylphenoly, 4-(trifluoromethyl)phenol, 4-hydroxybenzonitril, 1,2-dihydroxybenzene, 1,3-dihydroxybenzene, 1,4-dihydroxybenzene, methyl paraben, ethyl paraben or the isomers of xylenol.

Examples of preferred halogenated aliphatic alcohols are trifluoroethanol or trichloroethanol.

Examples of protonated aliphatic amines are hydrochloride salts of ethylamine, dimethylamine, diethylamine, diisopropylamine or triethylamine.

Examples of preferred thiols are ethanethiol, propanethiol, butanthiol or thiophenol.

In a preferred embodiment of the present invention the additive having a proton-donating functional group is selected from aromatic alcohols. In particular, the additive is selected from phenol, 2-methoxyphenol, 3-methoxyphenol, 4-methoxyphenol, 4-(trifluoromethyl)phenol, 4-hydroxybenzonitril, 1,3-dihydroxybenzene, 1,4-dihydroxybenzene and naphthalen-2-ol, especially phenol, 4-methoxyphenol, 1,4-dihydroxybenzene and naphthalen-2-ol.

Typically, the amount of additive used in the process according to the present invention is in the range of from 0.005 to 4 mol-%, preferably in the range of from 0.005 to 2 mol-%, based on the total amount of compound II in the reaction mixture.

More preferably, the amount of additive used in the process according to the present invention is in the range of from 0.005 to 1.5 mol-%, even more preferably in the range of from 0.01 to 1.0 mol-%, particularly in the range of from 0.02 to 0.8 mol-%, based on the total amount of compound II in the reaction mixture.

Suitable N-heterocyclic carbene catalysts used in the process according to the present invention are typically selected from compounds of the general formula V

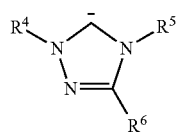

V in which $R^4$ and $R^5$ are independently selected from the group consisting of $C_1$-$C_6$-alkyl, aryl and heteroaryl, where aryl and heteroaryl are unsubstituted or substituted by 1, 2, 3 or 4 radicals selected from the group consisting of $C_1$-$C_4$-alkyl, $C_1$-$C_4$-haloalkyl, $C_1$-$C_4$-alkoxy and halogen;

$R^6$ is selected from the group consisting of $C_1$-$C_{12}$-alkyl, $C_1$-$C_{12}$-alkoxy, $C_1$-$C_6$-haloalkyl, —$NR^7R^8$, halogen, aryloxy, aryl and heteroaryl, where aryloxy, aryl and heteroaryl are unsubstituted or substituted by 1, 2, 3 or 4 radicals selected from the group consisting of $C_1$-$C_4$-alkyl, $C_1$-$C_4$-alkoxy and halogen;

$R^7$ is selected from the group consisting of hydrogen, $C_1$-$C_{12}$-alkyl and aryl;

$R^8$ is selected from the group consisting of $C_1$-$C_{12}$-alkyl and aryl;

or $R^5$ together with $R^6$ and the atoms to which they are bound form a fused, unsaturated N-heterocycle, which may be unsubstituted or substituted by 1, 2 or 3 radicals selected from the group consisting of $C_1$-$C_4$-alkyl, $C_1$-$C_4$-haloalkyl, $C_1$-$C_4$-alkoxy and halogen, and where the N-heterocycle is mono-, bi- or tricyclic, and where the N-heterocycle may have 1, 2 or 3 further heteroatoms as ring members, which are selected from O, S and N.

Preferably, the N-heterocyclic carbene catalyst used in the dimerization process of the present invention is selected from compounds of the general formula V, where $R^4$, $R^5$ and $R^6$ are independently selected from phenyl which can be optionally substituted by 1, 2, or 3 radicals selected from the group consisting of $C_1$-$C_4$-alkyl, $C_1$-$C_4$-alkoxy and halogen.

Examples of preferred radicals $R^4$, $R^5$ and $R^6$ are o-tolyl, m-tolyl, p-tolyl, 2,6-xylyl, 2,4-xylyl, 3,5-xylyl, mesityl, o-chlorophenyl, m-chlotophenyl, p-chlorophenyl, o-methoxyphenyl, m-methoxyphenyl, p-methoxyphenyl and the like.

Particularly preferred is a N-heterocyclic carbene catalyst of the general formula V, where the substituents $R^4$, $R^5$ and $R^6$ are phenyl.

In another embodiment of the present invention, the N-heterocyclic carbene catalyst is selected from compounds of formula V, where $R^4$ is as defined above, in particular phenyl, which can be optionally substituted by 1, 2, or 3 radicals selected from the group consisting of $C_1$-$C_4$-alkyl, $C_1$-$C_4$-alkoxy and halogen, and where $R^5$ together with $R^6$ and the atoms to which they are bound form a fused, unsaturated N-heterocycle, which may be unsubstituted or substituted by 1, 2 or 3 radicals selected from the group consisting of $C_1$-$C_4$-alkyl, $C_1$-$C_4$-haloalkyl, $C_1$-$C_4$-alkoxy and halogen, and where the N-heterocycle is mono-, bi- or tricyclic, and where the N-heterocycle may have 1, 2 or 3 further heteroatoms as ring members, which are selected from O, S and N. In particular $R^5$ together with $R^6$ and the atoms to which they are bound form a fused, unsaturated N-heterocycle, which has no further heteroatom such as fused pyridine, fused pyrimidine, fused pyridazine, fused quinoline, fused isoquinoline, fused quinazoline, fused cinnoline, fused phthalazine, fused quinoxaline, fused phenanthridine, fused benzo[h]quinoline, benzo[h]isoquinoline and fused phenanthroline. Examples are compounds of the general formulae V.1 to V.5

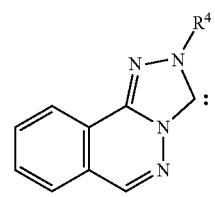

V.1

V.2

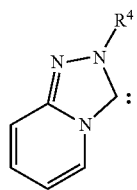

V.3

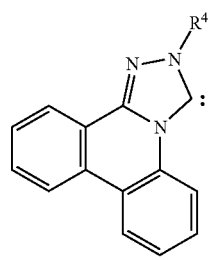

V.4

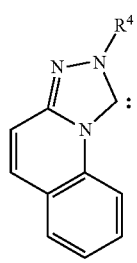

V.5 where $R^4$ is as defined above.

The N-heterocyclic carbene catalysts used in the dimerization process of the present invention can be prepared following procedures that are known in the art. Suitable methods for the generation of the N-heterocyclic carbene catalysts are for example described in EP 0587044 A2 and by Enders et al., Angew. Chem. Int. Ed. 1995, Vol. 34(9), pp. 1021-1023.

Typically, the N-heterocyclic carbene catalyst is generated in-situ from a methoxytriazolin precursor of the general formula (IV)

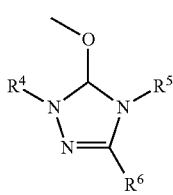

IV in which $R^4$, $R^5$ and $R^6$ are as defined above, by heating the precursor (IV) in the absence of any diluent under reduced pressure.

The pressure applied for the in-situ generation of the carbene catalyst V from precursor IV is preferably in the range from 0.01 to 10 mbar, in particular in the range from 0.1 to mbar.

The temperature used for the in-situ generation of the carbene catalyst V from precursor IV is in the range from 20 to 200° C., preferably from 40 to 160° C., in particular in the range from 50 to 110° C.

Generally, the N-heterocyclic carbene catalyst (V) is used in an amount from 0.1 to 10 mol-%, preferably 0.5 to 5 mol-%, based on the amount of compound II in the reaction mixture.

In a preferred embodiment of the present process, the dimerization reaction is performed in the presence of 0.005 to 3 mol % of additive and 0.5 to 5 mol % of N-heterocyclic carbene catalyst, based on the total amount of compound II.

In an even more preferred embodiment of the present process, the dimerization reaction is performed in the presence of 0.005 to 1.5 mol % of additive and 0.5 to 5 mol % of N-heterocyclic carbene catalyst, based on the total amount of compound II.

Regarding preferred and particularly preferred amounts of the additive and the N-heterocyclic carbine catalyst, reference is made to the definition given above.

The dimerization reaction is usually carried out in the temperature range from 20 to 200° C., preferably from 40 to 160° C., in particular in the range from 50 to 110° C.

The dimerization reaction can generally take place at ambient pressure or at reduced or elevated pressure. It is preferable that the dimerization reaction is carried out at ambient pressure or reduced pressure.

The dimerization reaction can be carried out in the absence of any added solvent or in the presence of an organic solvent.

If the dimerization reaction is carried out in the presence of a solvent, it is preferable that the organic solvent used is inert under the reaction conditions. Among these are by way of example aliphatic hydrocarbons, halogenated aliphatic hydrocarbons, and aromatic and substituted aromatic hydrocarbons and ethers. It is preferable that the solvent is one selected from pentane, hexane, heptane, ligroin, petrol ether, cyclohexane, dichloromethane, trichloromethane, tetrachloromethane, benzene, toluene, xylene, chlorobenzene, dichlorobenzenes, dibutyl ether, THF, 1,4-dioxane, 1,2-dimethoxyethane and mixtures thereof.

If the dimerization reaction is carried out in the presence of an inert organic solvent, the amount of the solvent in the reaction mixture is preferably less than 10% by weight, based on the amount of compound II.

The dimerization reaction can take place in the absence of or in the presence of an inert gas. The expression inert gas generally means a gas, which under the prevailing reaction conditions does not enter into any reactions with the starting materials, reagents, or solvents participating in the reaction, or with the resultant products. It is preferable that the dimerization reaction takes place without addition of any inert gas.

After completion of the dimerization reaction, any unconverted starting material (compound II) is preferably removed from the reaction mixture, e.g. by distillation. The distillation column necessary for this purpose generally has direct connection to the dimerization reactor, and it is preferable that said column is directly attached thereto. If desired, the recovered starting material (compound II) can be used for the next reaction.

Typically, the dimerization products are further purified by distillation or by using chromatographic methods. Preferably, the products I.a and I.b are purified by distillation.

The dimerization reaction of the present process provides the dimerization products I.a and I.b in high yields and selectivity. By way of example, for the dimerization of olefin compounds of the general formula II, where $R^2$ has one of the meanings given above and where $R^1$ is methyl, typically, no dimerization products of the general formula 1.c,

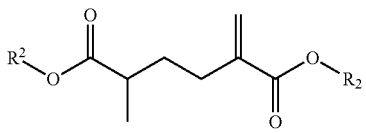

are detectable within the detection limits of the gas-chromatographic method used for analyzing the purity and composition of the dimerization products. The detection limit of the used gas-chromatographic analysis system is estimated to be about 10 wt.-ppm.

The examples below provide further explanation of the invention. These figures and examples are not to be understood as restricting the invention.

EXAMPLES

I) Gas Chromatographic (GC) Analysis

Sample preparation:

No special sample preparation was required and no solvent or diluent was used. The results were expressed as area-% resulting from an FID detector. The GC data were used to calculate the conversion of the starting material and the ratio of the isomers in the product. All yields given are isolated yields.

Gas chromatographic system and separation method:
GC-system: Agilent 6890
GC-Column: HP-5 (30 m (Length), 0.25 mm (ID), 0.25 μm (Film))
Temperature program: 40° C. for 10 min, 10° C./min to 190° C., 20° C./min to 300° C. for 10 min.

All pKa values given below were measured in water at 25° C. and are taken from literature (CRC Handbook of Tables for Organic Compound Identification, Third Edition, CRC Press, 1984/1979; E. P. Serjeant and B. Dempsey, Ionization Constants of Organic Acids in Aqueous Solution, Pergamon, N Y, 1979 or www.chemicalbook.com).

II) Production Examples

Example II.1 (Referential Example)

Generation of the N-heterocyclic carbene catalyst.

6.53 g 3-methoxy-2,4,5-triphenyl-3H-1,2,4-triazole (0.02 mol) was placed into a glass reactor equipped with heating jacket, mechanical stirrer and a vacuum line with implemented cold trap. The solid was heated at 80° C. for 20 hours under vacuum (ca. 1 mbar). The completion of the reaction can be confirmed by checking the expected weight loss. Within the indicated time the reaction is essentially complete. The resulting carbene catalyst was directly used for the dimerization reaction, without work-up or purification.

Example II.2 (Comparative Example)

Dimerization of Commercially Available Methyl Methacrylate without the Addition of an Additive.

To 0.02 mol of the carbene catalyst, prepared according to referential example II.1, 100 g methyl methacrylate (1.0 mol obtained from Aldrich Chemicals, containing ≤30 ppm of 4-methoxyphenol as stabilizer) was added. The resulting solution was then heated at 80° C. for 4 hours. The conversion of methyl methacrylate was approximately 50%. Unconverted methyl methacrylate was distilled off under reduced pressure and the remaining product was rectified (boiling point: 85° C. at <1 mbar) to obtain 48 g (48% yield) of a stereoisomer mixture of dimethylesters of 2,5-dimethyl-2-hexenedioic acid and 2,5-dimethyl-3-hexenedioic acid. The purity of the methylester composition was 99.7%. The purity and composition of the dimerization product was confirmed by using gas chromatography, GC/MS and $^1$H- and $^{13}$C-NMR.

Example II.3 (Comparative Example)

Dimerization of Additive Free Methyl Methacrylate without the Addition of an Additive.

To 0.02 mol of the carbene catalyst, prepared according to referential example II.1, 100 g methyl methacrylate (1.0 mol obtained from Aldrich Chemicals, freshly distilled over CaH$_2$ to remove the stabilizer) was added. The resulting solution was then heated at 80° C. for 4 hours. The methyl methacrylate conversion was approximately 25%. Unconverted methyl methacrylate was distilled off under reduced pressure and the remaining product was rectified (boiling point: 85° C. at <1 mbar) to obtain 23 g (23% yield) of a stereoisomer mixture of dimethylesters of 2,5-dimethyl-2-hexenedioic acid and 2,5-dimethyl-3-hexenedioic acid. The composition of the dimerization products was confirmed by using gas chromatography, GC/MS and $^1$H- and $^{13}$C-NMR.

Example II.4 (Comparative Example)

Dimerization of Methyl Methacrylate with n-Butanol (pKa=16.1) as Additive.

To 0.02 mol of the carbene catalyst, prepared according to referential example II.1, 100 g methyl methacrylate (1.0 mol obtained from Aldrich Chemicals, freshly distilled over CaH$_2$ to remove the stabilizer) and 18.5 g n-butanol (0.25 mol, 25 mol-%) were added. The resulting solution was then heated at 80° C. for 4 hours. The methyl methacrylate conversion was very low (7%). Unconverted methyl methacrylate was distilled off under reduced pressure and the remaining product was rectified (boiling point: 85° C. at <1 mbar) to obtain 4 g (4% yield) of a stereoisomer mixture of dimethyl esters of 2,5-dimethyl-2-hexenedioic acid and 2,5-dimethyl-3-hexenedioic acid. The composition of the dimerization products was confirmed by using gas chromatography, GC/MS and $^1$H- and $^{13}$C-NMR.

Example II.5

Dimerization of Methyl Methacrylate with Addition of 0.1 Weight-% of Hydroquinone (Pka$_{(1)}$=10.85, pKa$_{(2)}$=11.39).

To 0.02 mol of the carbene catalyst, prepared according to referential example II.1, 100 g methyl methacrylate (1.0 mol obtained from Aldrich Chemicals, containing ≤30 ppm of 4-methoxyphenol as stabilizer) and 0.1 g hydroquinone (0.9 mmol, 0.09 mol-%) were added. The resulting solution was then heated at 80° C. for 4 hours. The methyl methacrylate conversion was 88%. Unconverted methyl methacrylate was distilled off under reduced pressure and the remaining product was rectified (boiling point: 85° C. at <1 mbar) to obtain 86 g (86% yield) of a stereoisomer mixture of dimethylesters of 2,5-dimethyl-2-hexenedioic acid and 2,5-dimethyl-3-hexenedioic acid. The purity of the methylester composition was 99.7%. The purity and composition of the dimerization product was determined using gas chromatography, GC/MS and $^1$H- and $^{13}$C-NMR.

Example II.6

Dimerization of Methyl Methacrylate with Addition of 0.1 Weight-% of Phenol (pKa=9.99).

To 0.02 mol of the carbene catalyst, prepared according to referential example II.1, 100 g methyl methacrylate (1.0 mol obtained from Aldrich Chemicals, containing ≤30 ppm of 4-methoxyphenol as stabilizer) and 0.1 g phenol (1.1 mmol) were added. The resulting solution was then heated at 80° C. for 4 hours. The methyl methacrylate conversion was 89%. Unconverted methyl methacrylate was distilled off under reduced pressure and the remaining product was rectified (boiling point: 85° C. at <1 mbar) to obtain 87 g (87% yield) of a stereoisomer mixture of dimethylesters of 2,5-dimethyl-2-hexenedioic acid and 2,5-dimethyl-3-hexenedioic acid. The purity of the methylester composition was 99.7%. The purity and composition of the dimerization product was determined using gas chromatography, GC/MS and $^1$H- and $^{13}$C-NMR.

Example II.7 (Comparative Example)

Dimerization of Commercial Ethyl Methacrylate without the Addition of an Additive.

To 0.02 mol of the carbene catalyst, prepared according to referential example II.1, 115.3 g ethyl methacrylate (1.0 mol obtained from Aldrich Chemicals, containing 15-20 ppm of 4-methoxyphenol as stabilizer) was added. The resulting solution was then heated at 80° C. for 4 hours. The ethyl methacrylate conversion was very low (<5%). Unconverted ethyl methacrylate was distilled off under reduced pressure and the remaining product was rectified (boiling point: 93° C. at <1 mbar) to obtain 2.3 g (2% yield) of a stereoisomer mixture of diethylesters of 2,5-dimethyl-2-hexenedioic acid and 2,5-dimethyl-3-hexenedioic acid. The composition of the dimerization products was determined using gas chromatography, GC/MS and $^1$H- and $^{13}$C-NMR.

Example II.8

Dimerization of Commercial Ethyl Methacrylate with Addition of 0.1 Weight-% of Hydroquinone (Pka$_{(1)}$=10.85, pKa$_{(2)}$=11.39).

To 0.02 mol of the carbene catalyst, prepared according to referential example II.1, 115.3 g ethyl methacrylate (1.0 mol obtained from Aldrich Chemicals, containing 15-20 ppm of 4-methoxyphenol as stabilizer) and 0.12 g hydroquinone (1.1 mmol) were added. The resulting solution was then heated at 80° C. for 4 hours. The ethyl methacrylate conversion was 80%. Unconverted ethyl methacrylate was distilled off under reduced pressure and the remaining product was rectified (boiling point: 93° C. at <1 mbar) to obtain 89.7 g (78% yield) of a stereoisomer mixture of diethylesters of 2,5-dimethyl-2-hexenedioic acid and 2,5-dimethyl-3-hexenedioic acid. The purity of the diethylester isomer mixture was 97.1%. The product contained 2.3% of the methyl-ethyl ester as the major impurity stemming from the ca. 1% methyl methacrylate contained as impurity in the ethyl methacrylate used. The purity and composition of the dimerization products was determined using gas chromatography, GC/MS and $^1$H- and $^{13}$C-NMR.

Example II.9 (Comparative Example)

Dimerization of Commercial n-Butyl Methacrylate without the Addition of an Additive.

To 0.02 mol of the carbene catalyst, prepared according to referential example II.1, 143.6 g n-butyl methacrylate (1.0 mol obtained from Aldrich Chemicals, containing 10 ppm of 4-methoxyphenol as stabilizer) was added. The resulting solution was then heated at 80° C. for 4 hours. The n-butyl methacrylate conversion was low (ca. 10%). Unconverted n-butyl methacrylate was distilled off under reduced pressure and the remaining product was rectified (boiling point: 136° C. at <1 mbar) to obtain 13.5 g (9.5% yield) of a stereoisomer mixture of di-(n-butyl)esters of 2,5-dimethyl-2-hexenedioic acid and 2,5-dimethyl-3-hexenedioic acid. The purity of the n-butylester isomer mixture was 99.8%. The purity and composition of the dimerization products was determined using gas chromatography, GC/MS and $^1$H- and $^{13}$C-NMR.

Example II.10

Dimerization of n-Butyl Methacrylate with Addition of 0.1 Weight-% of Hydroquinone (Pka$_{(1)}$=10.85, pKa$_{(2)}$=11.39).

To 0.02 mol of the carbene catalyst, prepared according to referential example II.1, 143.6 g n-butyl methacrylate (1.0 mol obtained from Aldrich Chemicals, containing 10 ppm of 4-methoxyphenol as stabilizer) and 0.14 g hydroquinone (1.3 mmol) were added. The resulting solution was then heated at 80° C. for 4 hours. The n-butyl methacrylate conversion was 70%. Unconverted n-butyl methacrylate was distilled off under reduced pressure and the remaining product was rectified (boiling point: 136° C. at <1 mbar) to obtain 96.6 g (68.3% yield) of a stereoisomer mixture of di-(n-butyl)esters of 2,5-dimethyl-2-hexenedioic acid and 2,5-dimethyl-3-hexenedioic acid. The purity of the n-butyl ester isomer mixture was 99.8%. The purity and composition of the dimerization products was determined using gas chromatography, GC/MS and $^1$H- and $^{13}$C-NMR.

Examples II.11 to II.19 (Examples II.11 and II.12 are Comparative Examples)

Dimerization of Methyl Methacrylate in the Presence Different Amounts of 4-Methoxyphenol (pKa=10.2) as Additive.

To 0.015 mol of the carbene catalyst, prepared according to referential example II.1, 100 g methyl methacrylate (1.0 mol obtained from Aldrich Chemicals and distilled before use over CaH$_2$ to remove the stabilizer, for example 12 the methyl methacrylate was additionally stored over mol sieves before use) and different amounts of 4-methoxyphenol (pKa=10.2, obtained from Aldrich Chemicals, the mol-% are relative to the methyl methacrylate) were added. The resulting solution was then heated at 80° C. and samples were taken at regular intervals, quenched by adding a drop of trifluoroacetic acid and analyzed by GC to determine the methyl methacrylate conversion. The dimethyl esters of 2,5-dimethyl-2-hexenedioic acid and 2,5-dimethyl-3-hexenedioic acid were the only products formed. The conversions as a function of the reaction time and the concentration of the 4-methoxyphenol are given in table 1.

TABLE 1

Conversion of methyl methacrylate

| Example | Additive [Mol-%] | 0 | 1 | 2 | 3 | 4 | 5 | 6 |
|---|---|---|---|---|---|---|---|---|
| 11 [1)] | 0 | 0 | 14 | 21 | 23 | 25 | 30 | 32 |
| 12 [1)] | 0 | 0 | 7 | 7 | 7 | 8 | 8 | 12 |
| 13 | 0.01 | 0 | 48 | 72 | 81 | 86 | 89 | 91 |
| 14 | 0.02 | 0 | 53 | 71 | 84 | 89 | 92 | 95 |
| 15 | 0.05 | 0 | 59 | 79 | 88 | 91 | 95 | 96 |
| 16 | 0.10 | 0 | 59 | 77 | 83 | 88 | 92 | 94 |
| 17 | 0.20 | 0 | 58 | 74 | 82 | 87 | 90 | 92 |
| 18 | 0.50 | 0 | 44 | 58 | 67 | 72 | 76 | 79 |
| 19 | 1.50 | 0 | 50 | 60 | 70 | 70 | 74 | 82 |

[1)] Comparative examples

Examples II.20 to II.24

Dimerization of Methyl Methacrylate in the Presence Different Amounts of Phenol (pKa=9.99) as Additive.

The same procedure was used as in examples II.11 to II.19 but using phenol (pK$_a$=9.99, obtained from Aldrich Chemicals) as the additive. The amounts of phenol used in each experiment and the methyl methacrylate conversions observed are shown in table 2.

TABLE 2

Conversion of methyl methacrylate

| Example | Additive [Mol %] | 0 | 1 | 2 | 3 | 4 | 5 |
|---|---|---|---|---|---|---|---|
| 20 | 0.02 | 0 | 63 | 79 | 89 | 93 | 94 |
| 21 | 0.10 | 0 | 61 | 77 | 82 | 86 | 89 |
| 22 | 0.20 | 0 | 65 | 79 | 90 | 87 | 89 |
| 23 | 0.50 | 0 | 56 | 72 | 83 | 83 | 86 |
| 24 | 1.50 | 0 | 53 | 67 | 78 | 73 | 75 |

Examples II.25 to II.29

Dimerization of Methyl Methacrylate in the Presence Different Amounts of 2-Naphtol (pKa=9.57) as Additive.

The same procedure was used as in examples II.11 to II.19 but using 2-naphtol (pK$_a$=9.57, obtained from Aldrich Chemicals) as the additive. The amounts of 2-naphtol used in each experiment and the methyl methacrylate conversions observed are shown in table 3.

TABLE 3

Conversion of methyl methacrylate

| Example | Additive [Mol %] | 0 | 1 | 2 | 3 | 4 | 5 |
|---|---|---|---|---|---|---|---|
| 25 | 0.02 | 0 | 55 | 78 | 85 | 89 | 92 |
| 26 | 0.10 | 0 | 58 | 75 | 83 | 86 | 90 |
| 27 | 0.20 | 0 | 54 | 78 | 83 | 86 | 89 |
| 28 | 0.50 | 0 | 55 | 70 | 74 | 80 | 85 |
| 29 | 1.50 | 0 | 47 | 59 | 70 | 72 | 72 |

Examples II.30 to II.34

Dimerization of Methyl Methacrylate in the Presence Different Amounts of 4-Trifluoromethyl-Phenol (pKa=8.7) as Additive.

The same procedure was used as in examples II.11 to II.19 but using 4-trifluoromethyl-phenol (pK$_a$=8.7, obtained from Aldrich Chemicals) as the additive. The amounts of 4-trifluoromethyl-phenol used in each experiment and the methyl methacrylate conversions observed are shown in table 4.

TABLE 4

Conversion of methyl methacrylate

| Example | Additive [Mol %] | 0 | 1 | 2 | 3 | 4 | 5 |
|---|---|---|---|---|---|---|---|
| 30 | 0.02 | 0 | 49 | 70 | 78 | 77 | 85 |
| 31 | 0.10 | 0 | 59 | 75 | 84 | 87 | 94 |
| 32 | 0.20 | 0 | 52 | 78 | 82 | 87 | 90 |
| 33 | 0.50 | 0 | 48 | 72 | 81 | 80 | 92 |
| 34 | 1.50 | 0 | 42 | 67 | 73 | 75 | 81 |

Examples II.35 to II.39

Dimerization of Methyl Methacrylate in the Presence Different Amounts of 4-Hydroxybenzonitrile (pKa=7.8) as Additive.

The same procedure was used as in examples II.11 to II.19 but using 4-hydroxybenzonitrile (pK$_a$=7.8, obtained from Aldrich Chemicals) as the additive. The amounts of 4-hydroxybenzonitrile used in each experiment and the methyl methacrylate conversions observed are shown in table 5.

TABLE 5

Conversion of methyl methacrylate

| Example | Additive [Mol %] | 0 | 1 | 2 | 3 | 4 | 5 |
|---|---|---|---|---|---|---|---|
| 35 | 0.02 | 0 | 36 | 45 | 52 | 53 | 56 |
| 36 | 0.10 | 0 | 51 | 66 | 79 | 83 | 84 |
| 37 | 0.20 | 0 | 48 | 65 | 82 | 85 | 87 |
| 38 | 0.50 | 0 | 47 | 67 | 80 | 83 | 84 |
| 39 | 1.50 | 0 | 34 | 57 | 62 | 70 | 74 |

Examples II.40 to II.44

Dimerization of Methyl Methacrylate in the Presence Different Amounts of 2,6-Di-Tert Butyl-4-Methylphenol (pKa=12.75) as Additive.

The same procedure was used as in examples II.11 to II.19 but using 2,6-di-tert-butyl-4-methylphenol (pK$_a$=12.75, obtained from Aldrich Chemicals) as the additive. The amounts of 2,6-di-tert-butyl-4-methylphenol used in each experiment and the methyl methacrylate conversions observed are shown in table 6.

TABLE 6

Conversion of methyl methacrylate

| Example | Additive [Mol %] | 0 | 1 | 2 | 3 | 4 | 5 |
|---|---|---|---|---|---|---|---|
| 40 | 0.02 | 0 | 11 | 18 | 29 | 38 | 41 |
| 41 | 0.10 | 0 | 17 | 28 | 40 | 48 | 58 |
| 42 | 0.20 | 0 | 16 | 25 | 33 | 45 | 53 |

TABLE 6-continued

Conversion of methyl methacrylate

| Example | Additive [Mol %] | Reaction time [h] | | | | |
|---|---|---|---|---|---|---|
| | | 0 | 1 | 2 | 3 | 4 | 5 |
| 43 | 0.50 | 0 | 27 | 40 | 49 | 58 | 67 |
| 44 | 1.50 | 0 | 49 | 51 | 74 | 74 | 83 |

Examples II.45 to II.47 (Comparative)

Dimerization of Methyl Methacrylate in the Presence Different Amounts of Water (pKa=15.7) as Additive.

The same procedure was used as in examples II.11 to II.19 but using deionized water ($pK_a$=15.7) as the additive. The amounts of water used in each experiment and the methyl methacrylate conversions observed are shown in table 7.

TABLE 7

Conversion of methyl methacrylate

| Example | Additive Mol % | Reaction time/h | | | | | |
|---|---|---|---|---|---|---|---|
| | | 0 | 1 | 2 | 3 | 4 | 5 |
| 45 [1] | 0.02 | 0 | 7 | 9 | 9 | 9 | 11 |
| 46 [1] | 0.10 | 0 | 6 | 8 | 17 | 10 | 10 |
| 47 [1] | 1.50 | 0 | 0 | 9 | 9 | 14 | 15 |

[1] Comparative examples

The invention claimed is:

1. A process for preparing a compound or a mixture of compounds of the general formulae I.a or I.b

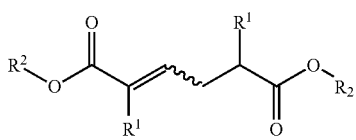

I.a

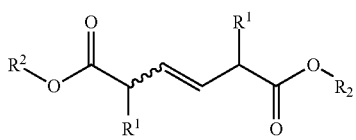

I.b wherein
R$^1$ is selected from the group consisting of C$_1$-C$_{12}$-alkyl, C$_3$-C$_6$-cycloalkyl, —C(=O)OR$^2$, —PO(OR$^{2a}$)$_2$, aryl and hetaryl,
R$^2$, R$^{2a}$ are independently of each other selected from the group consisting of hydrogen, C$_1$-C$_{12}$-alkyl, —C$_2$-C$_{12}$ alkenyl-, wherein the last two radicals mentioned are unsubstituted, partly or completely halogenated or substituted by 1, 2, 3 or 4 radicals selected from the group consisting of C$_1$-C$_6$-alkoxy and CN, C$_3$-C$_6$-cycloalkyl, C$_3$-C$_6$-cycloalkyl-C$_1$-C$_4$-alkyl, aryl and aryl-C$_1$-C$_4$-alkyl, wherein the last four radicals mentioned are unsubstituted or substituted by 1, 2, 3 or 4 radicals selected from the group consisting of C$_1$-C$_6$-alkyl, C$_1$-C$_6$-haloalkyl, C$_1$-C$_6$-alkoxy, C$_1$-C$_6$-haloalkoxy, —CN, and halogen,
the process comprising dimerizing olefin compound of the general formula II,

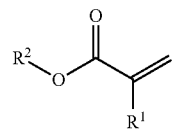

II in the presence of at least one N-heterocyclic carbene catalyst selected from compounds of the general formula V

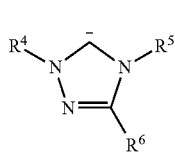

V in which
R$^4$ and R$^5$ are independently selected from the group consisting of C$_1$-C$_6$-alkyl, aryl and heteroaryl, wherein aryl and heteroaryl are unsubstituted or substituted by 1, 2, 3 or 4 radicals selected from the group consisting of C$_1$-C$_4$-alkyl, C$_1$-C$_4$-alkoxy and halogen;
R$^6$ is selected from the group consisting of C$_1$-C$_{12}$-alkyl, C$_1$-C$_{12}$-alkoxy, C$_1$-C$_6$-haloalkyl, —NR$^7$R$^8$, halogen, aryloxy, aryl and heteroaryl, wherein aryloxy, aryl and heteroaryl are unsubstituted or substituted by 1, 2, 3 or 4 radicals selected from the group consisting of C$_1$-C$_4$-alkyl, C$_1$-C$_4$-alkoxy and halogen;
R$^7$ is selected from the group consisting of hydrogen, C$_1$-C$_{12}$-alkyl and aryl;
R$^8$ is selected from the group consisting of C$_1$-C$_{12}$-alkyl and aryl;
or R$^5$ together with R$^6$ and the atoms to which they are bound form a fused, unsaturated N-heterocycle, which is unsubstituted or substituted by 1, 2 or 3 radicals selected from the group consisting C$_1$-C$_4$-alkyl, C$_1$-C$_4$-haloalkyl, C$_1$-C$_4$-alkoxy and halogen, and wherein the N-heterocycle is mono-, bi- or tricyclic, and wherein the N-heterocycle optionally has 1, 2 or 3 further heteroatoms as ring members, which are selected from O, S and N, and in the presence of at least one additive having at least one proton donating functional group, wherein the additive is used in an amount of from 0.005 to 4 mol-%, based on the total amount of compound (II) in the reaction mixture, and wherein the proton-donating functional group has a pKa-value in water at 25° C. in the range of from 4 to 14, to yield a compound of the general formulae I.a or I.b or a mixture thereof.

2. The process of claim 1, wherein the additive is used in an amount of from 0.005 to 1.5 mol-%, based on the total amount of compound (II) in the reaction mixture.

3. The process of claim 1, wherein the radical R$^1$ in formulae I.a, I.b and II is selected from unsubstituted C$_1$-C$_4$-alkyl.

4. The process of claim 1, wherein R$^2$ is selected from unsubstituted C$_1$-C$_6$-alkyl.

5. The process of claim 1, wherein in formulae I.a, I.b and II, both R$^2$ are identical.

6. The process of claim 1, wherein the compound of formula II is selected from the group consisting of methyl methacrylate, ethyl methacrylate and n-butyl methacrylate.

7. The process of claim 1, wherein the proton-donating functional group has a pKa-value in water at 25° C. in the range of from 7 to 13.

8. The process of claim 1, wherein the additive is selected from the group consisting of aromatic alcohols, halogenated aliphatic alcohols, protonated aliphatic amines and thiols.

9. The process of claim 1, wherein the additive is an aromatic alcohol.

10. The process of claim 1, wherein the additive is selected from the group consisting of phenol, 2-methoxyphenol, 3-methoxyphenol, 4-methoxyphenol, 4-(trifluoromethyl)phenol, 4-hydroxybenzonitril, 1,3-dihydroxybenzene, 1,4-dihydroxybenzene and naphthalen-2-ol.

11. The process of claim 1, wherein the additive is selected from the group consisting of phenol, 4-methoxyphenol, 1,4-dihydroxybenzene and naphthalen-2-ol.

12. The process of claim 1, wherein in formula V, $R^4$, $R^5$ and $R^6$ are independently selected from phenyl which is optionally substituted by 1, 2, or 3 radicals selected from the group consisting of $C_1$-$C_4$-alkyl, $C_1$-$C_4$-alkoxy and halogen.

13. The process of claim 12, wherein the N-heterocyclic carbene catalyst is generated in-situ from a compound of the general formulae

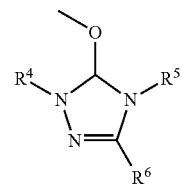

IV wherein $R^4$, $R^5$ and $R^6$ are as defined in claim 1.

14. The process of claim 1, wherein the N-heterocyclic carbene catalyst is used in an amount of from 0.1 to 10 mol-%, based on the total amount of compound II.

15. The process of claim 1, wherein the dimerization reaction is performed in the presence of less than 10 weight-%, based on the total amount of compound II, of an inert organic solvent.

16. The process of claim 1, wherein the dimerization reaction is performed in the presence of 0.005 to 1.5 mol % of additive and 0.5 to 5 mol % of N-heterocyclic carbene catalyst, based on the total amount of compound II.

17. The process of claim 1, wherein the radical $R^1$ in formulae I.a, I.b and II is methyl.

* * * * *